United States Patent [19]

Fry et al.

[11] Patent Number: 4,852,596
[45] Date of Patent: Aug. 1, 1989

[54] MICRO SLIDE IRRIGATING UNIT

[75] Inventors: David M. Fry; Sharon A. Fry, both of Faber, Va.

[73] Assignee: The University of Virginia Alumni Patents Foundation, Charlottesville, Va.

[21] Appl. No.: 217,124

[22] Filed: Jul. 7, 1988

Related U.S. Application Data

[63] Continuation of Ser. No. 48,467, May 8, 1987, abandoned, which is a continuation of Ser. No. 917,494, Oct. 10, 1986, abandoned, which is a continuation of Ser. No. 720,274, Apr. 5, 1986, abandoned.

[51] Int. Cl.$^4$ .............................................. B08B 3/04
[52] U.S. Cl. .................................... 134/182; 134/201
[58] Field of Search ............... 134/108, 111, 155, 182, 134/186, 195, 198, 199, 200, 201; 68/181 R, 195; 354/324, 326

[56] References Cited

U.S. PATENT DOCUMENTS 784,861  3/1905  Johnson ............................ 134/155

Primary Examiner—Philip R. Coe
Attorney, Agent, or Firm—James C. Wray

[57] ABSTRACT

A slide irrigating unit has two plexiglass boxes, an inner box forming an irrigating chamber and an outer box forming a drain box. The outer drain box is tightly sealed and its inner walls form the perimeters of the inner box which is open at the top. PVC tubing extends through the outer box and underneath the inner box. This tubing is attached to a fresh water source. The fresh water flows into this PVC tubing and under the bottom of the inner box. Water emerges from this PVC tubing through holes in the bottom of the inner box. As the water level increases in height, it rinses racks of stained microscopic slides that have been inserted into the inner box from the top. The inner box contains drainage holes approximately one inch from the top of the open inner box. The stain contaminated water rises from the bottom of the inner box and drains through these drainage holes into the sealed outer box. The stain contaminated water exits the outer drain box through a PVC drainage pipe in the bottom of the outer box. By attaching a tube to this drainage pipe, one can drain the stain contaminated water directly into the drain of a sink.

17 Claims, 3 Drawing Sheets

MICRO SLIDE IRRIGATING UNIT

This application is a continuation of application Ser. No. 048,467, filed May 8, 1987, now abandoned, which in turn is a continuation of application Ser. No. 917,494, filed Oct. 10, 1986, now abandoned, which in turn is a continuation of application Ser. No. 720,274, filed Apr. 5, 1985, now abandoned.

BACKGROUND OF THE INVENTION

The present invention relates to the preparation of microscope slides and more specifically to an apparatus for rinsing and washing slides during their various staining procedures.

Complete rinsing is essential to slide preparation. A problem persists in the art in that washing or rinsing devices currently available cannot effect complete rinsing for a number of slides simultaneously in a short period of time. Incomplete washing and/or rinsing can result in cross-contamination between slides.

SUMMARY OF THE INVENTION

The present invention thoroughly and gently rinses microscopic slides during their various staining procedures. The unit consists of two boxes, one within the other, with built-in tubing that allows a constant supply of fresh water to enter the inner box from the bottom engulfing the slides as the water rises to the top of the inner box where it drains through holes to be collected in the outer box which is emptied through a drain in the bottom. As the stain-free water entering the inner box from the bottom passes through the staining racks, it forces the contaminated water to the surface and out of the holes in the inner box which acts as an irrigating chamber into the outer box which acts as a drain box and empties into the sink drain never to come into contact with the slides again.

Since the tissue covered slides are at all times being irrigated with fresh water, the rinsing time is cut drastically from five to ten minutes to a matter of thirty to forty seconds. This cleaning system creates a minimal amount of cross-contamination when various stains are used at one time. The device is a self-contained unit with no moving parts. Only water soluble stains, dyes, and solutions can be used with the present invention. It is not capable of rinsing harsh solvents such as xylene or toluene, due to its construction, in part, from plexiglass and plexiglass glues.

Preferably, the materials used are plexiglass sheets, ¼ inch thick, forming the walls, bottom and top of the unit. PVC tubing is used for the water system in the unit. The plexiglass pieces are held together using plexiglass epoxy and glue. The unit can be manufactured and shipped pre-assembled. There are no moving parts in the assembled units.

Basically, the invention uses a box within a box and is designed primarily to increase the speed with which microscopic slides that have been stained with various staining procedures, can be rinsed. The unit rinses the stained slides from the bottom up allowing a constant supply of fresh water to engulf the slides. Fresh stain-free water passes through the racks of stained slides from the bottom up. This forces the contaminated water to the surface of the inner box which then drains into the sealed outer box. A drain pipe from the outer box allows drainage directly into sink drains.

DETAILED DESCRIPTION OF THE DRAWINGS

Figure 1:
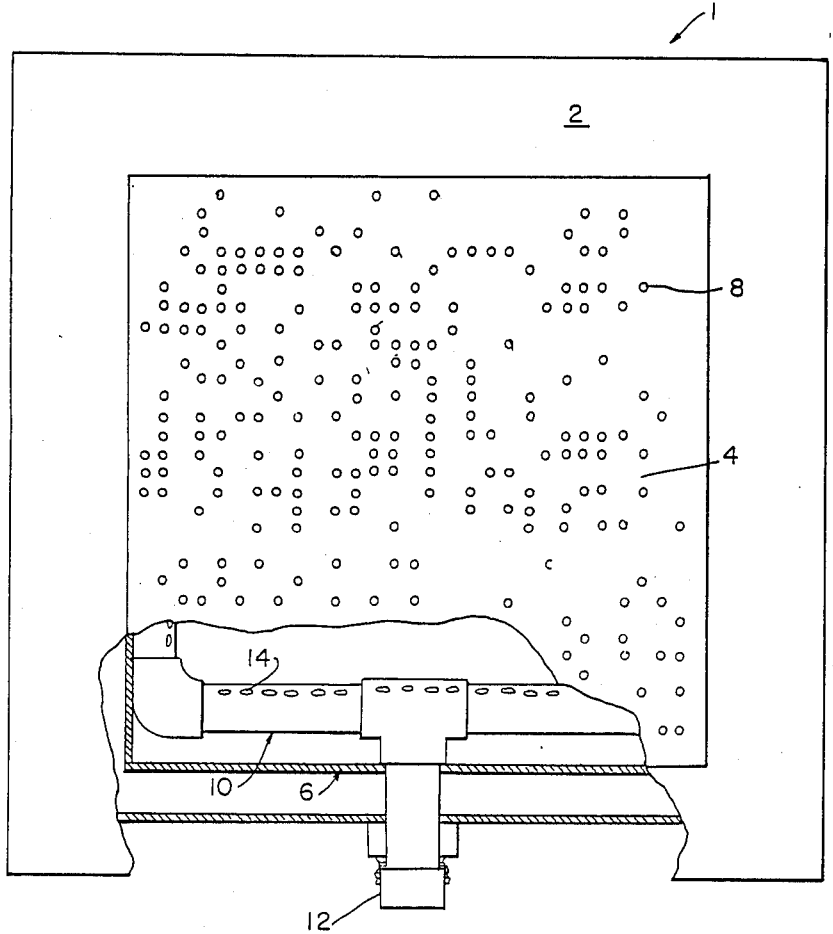
FIG. 1 is a top view, partially in section, of a preferred embodiment of the invention.

Referring to FIG. 1, the micro-slide irrigating unit is generally referred to as numeral 1. The unit has a counter top flange 2 which is rectangular with a rectangular opening which provides access to the interior of the unit.

From above, an irrigating shelf 4 is visible. The shelf 4 constitutes a bottom of irrigation chamber 6. The shelf 4 is provided with a plurality of apertures 8. The shelf carries staining racks that are filled with stained microscopic slides (not shown in FIG. 1).

An irrigation coil 10 is preferably made of PVC piping and is connected to a fresh water source through extension pipe 12. The coil 10 is provided with apertures 14 equidistantly spaced along the top of the coil.

Figure 2:
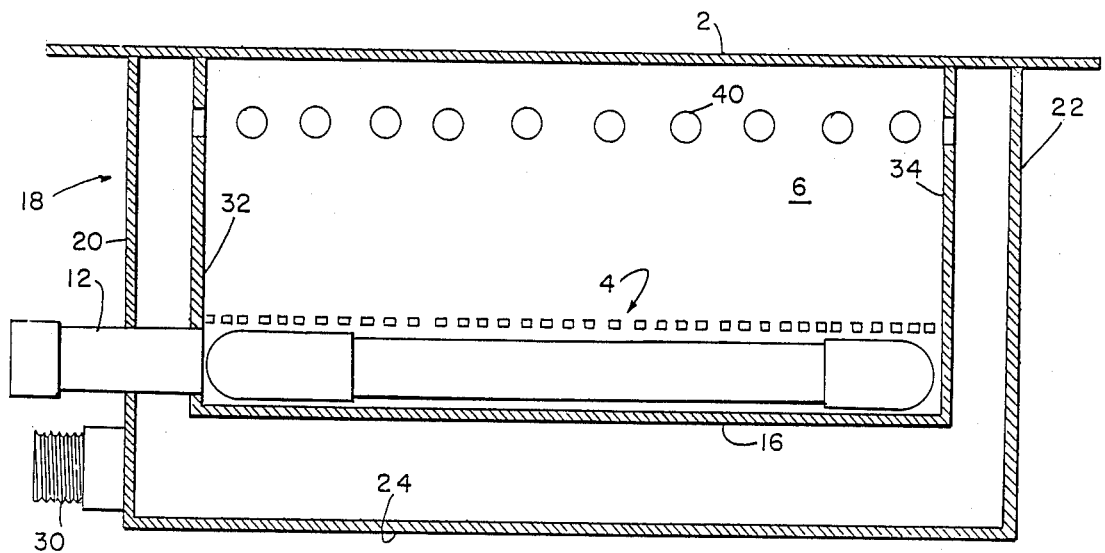
FIG. 2 is a side view, partially in section, of the embodiment of FIG. 1.

The coil 10 lies directly beneath the irrigation shelf 4, as shown in FIG. 2 and is disposed between the shelf and a bottom 16 of the irrigation chamber, which basically comprises a box-like structure having four sides, a bottom and an open top. When assembled, the shelf 4 acts as a bottom for the irrigation chamber 6, although the apertures in the shelf allow for fluid passage from coil 10 into the irrigation chamber, as will be described in greater detail.

In a preferred embodiment, the PVC pipe used in making the coil has one quarter inch holes drilled one-half inch apart along its top and lies directly underneath the irrigation shelf. As fresh water enters the extension pipe and flows through the irrigation coil, it is forced out the top of the coil and consequently forced through the irrigation shelf. As more water flows through the irrigation coil, the level of water in the irrigation chamber or inner box rises.

The fresh water rises through the racks of stained microscopic slides (placed on the shelf 4) and carries off the stain of the slides. As the fresh water level rises in the irrigation chamber, it becomes stain contaminated on its way up to the top of the irrigation chamber. A drainage system is provided and can best be illustrated in FIGS. 2 and 3.

Figure 3:
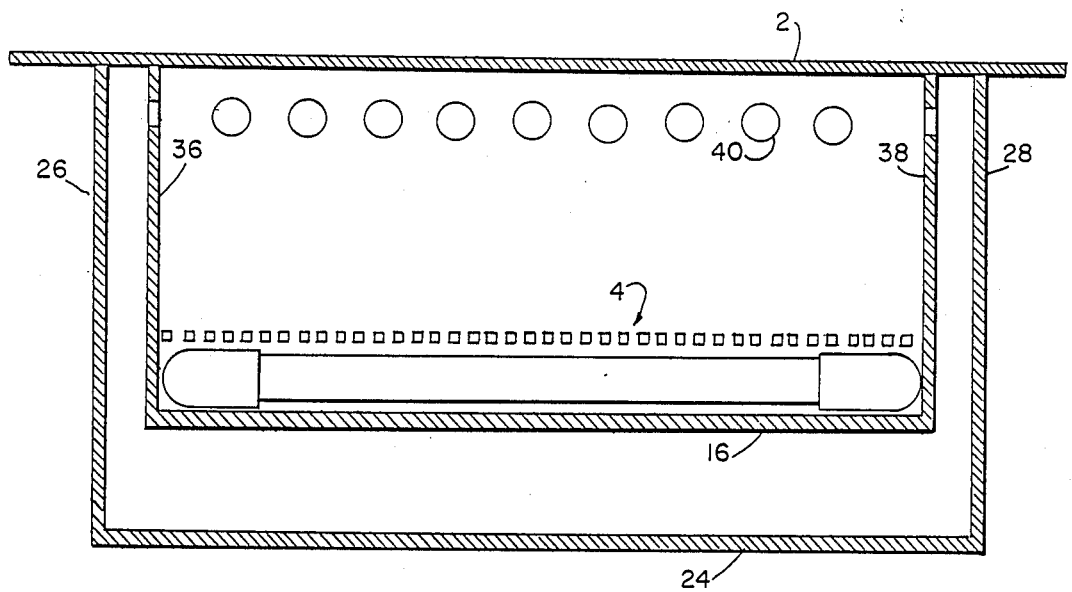
FIG. 3 is a rear view, partially in section, of the embodiment of FIG. 1.

Referring to FIG. 2, a drain box is generally referred to by the numeral 18. The drain box has a front wall 20, a rear wall 22 and a bottom 24. Side walls 26, 28 are shown in FIG. 3.

Referring back to FIG. 2, drain box 18 is provided with a drain pipe 30 at a lower portion of the front wall 20.

Irrigation chamber 6 also has a front wall 32, a rear wall 34, and bottom 16. Extension pipe 12 acts as a water inlet and is disposed at a lower portion of front wall 32. Side walls 36, 38 are shown in FIG. 3. The drain pipe 30 allows water from the drain box to be drained into a pre-existing sink drain (not shown).

The extension pipe 12 extends from outside the device through the drain box 18 or outer box and conects with the irrigation coil 10. The extension pipe is connected to a fresh water source and allows the fresh water to flow through the walls of the outer box and into the coil so that fresh water can emerge out the top of the irrigation coil and enter the bottom of the irrigation chamber or inner box through the irrigation shelf.

The drain box 18 collects the stain-contaminated water which enters the drain box from an upper portion thereof through drain holes 40 provided in the top of the walls of the inner box or irrigation chamber 6. The drain box drains through drain pipe 30 thereby allowing contaminated water to drain through and into a hose (not shown) which could preferably be connected to a pre-existing drain in a sink.

The flange 2 can be made of one-quarter inch plexiglass. The flange may be two inches in width and serves as the top sealing, sealing the outer box or drain box 18. It is attached to the walls of the outer box and can be used to lift the unit. Preferably, it extends over the walls of the outer box by one-half inch on all sides.

In the preferred embodiment, all of the walls of the drain box and irrigation chamber, including the bottoms and the shelf, can be made of quarter-inch plexiglass panels attached at the corners and sides by epoxy glue and plexiglass glue.

Since the flange 2 is only about two inches in width, it is only intended to cover the area between the walls of the drain box 18 and the irrigation chamber 6 so as to leave open an area at the top so that racks of microscopic slides containing stain can be placed into the irrigation chamber.

The holes 40 in the walls of the irrigation chamber allow the stain contaminated water being forced up inside the irrigation chamber to flow out of the chamber into the self-contained drain box.

The flow of water is through the extension pipe 12 into the irrigation coil 10, up through the irrigation shelf 4, continuing upward until drained through holes 40, collecting in the drain box 18 and then draining out through drain pipe 30.

Water entering through coil 10 will rise upwardly through the holes 8 of the shelf 4 filling the entire irrigation chamber from the bottom up until drained through holes 40.

Figure 4:
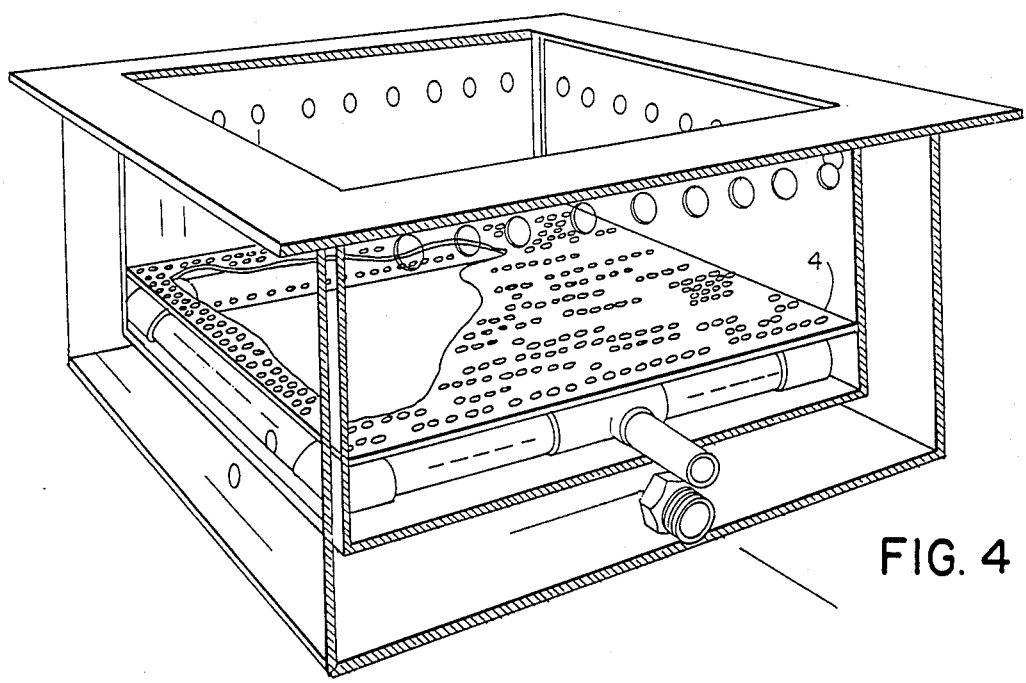
FIG. 4 is an exposed perspective view of the embodiment of FIG. 1.

FIG. 4 shows the flow of water through the unit indicating the method and function in which the slides are rinsed.

The irrigation shelf is preferably made of one-quarter inch plexiglass and measures ten by ten inches. The shelf 4 supports slide racks (shown in FIG. 5) of microscopic slides that have been stained with various staining solutions. During use of the invention, the slide racks will be placed within the irrigation chamber and will rest on the shelf 4.

Arrows have been provided in FIG. 4 to illustrate the fluid flow path through the unit.

As water is forced through the irrigation coil and through the holes in the irrigation shelf because of water pressure, it will fill the irrigation chamber from the bottom up. The water flows up through the bottom of the slide rack trays, rinsing the slides as the water is forced upwardly. This will cause the stain contaminated water to be pushed upwardly ahead of the fresh water that is being forced into the unit from the bottom.

Figure 5:
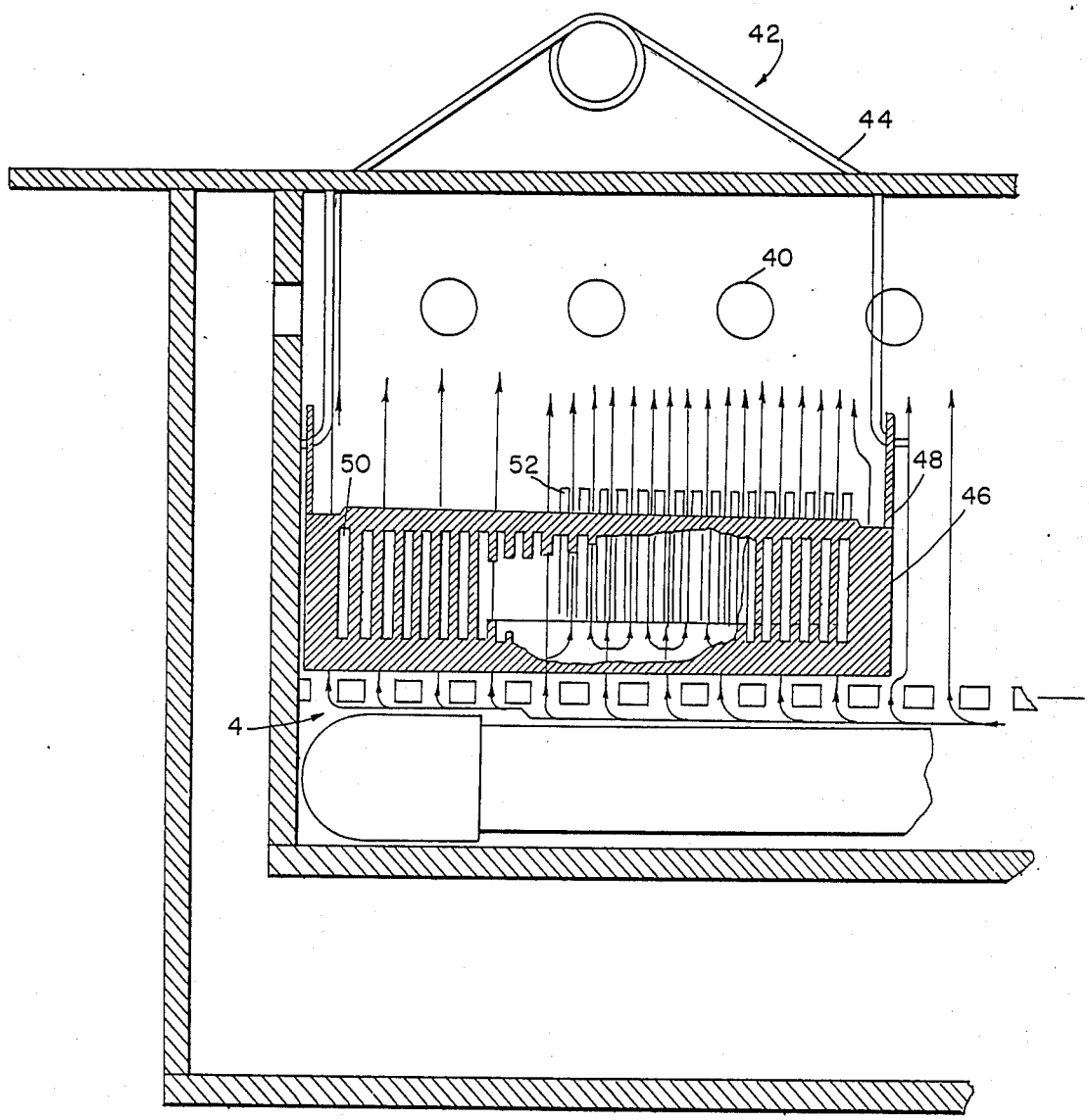
FIG. 5 is a detailed sectional view of the preferred embodiment containing a slide tray.

Details of the slide tray 42 are shown in FIG. 5. Generally, the tray 42 has a handle 44 pivotally connected to a slide holding portion 46 through support arms 48. A plurality of slots 50, parallel and equidistantly spaced, provide means for supporting slides 52 in vertical spaced relation.

As shown, the tray 42 rests on the shelf 4. The arrows demonstrate that water from the coil 10 rises up through apertures in the shelf 4, through the bottom of the tray and between the individual slides.

In the preferred embodiment, the holes 40 are drilled one inch from the top of the irrigation chamber.

The slide tray 42 contains the microscopic slides that have been inundated with various stains necessary for increasing the visual perception of various aspects of microscopic specimens. The slide trays are open at the bottom allowing the water which is rising upwards in the mechanism to flow up along the microscopic slides. This allows the fresh water to rinse off the excess stain. The stain contaminated water is forced upwards in the irrigation chamber from the pressure of the fresh water being forced into the irrigation chamber from the bottom through the irrigation coil and irrigation shelf. The stain contaminated water drains from the top of the irrigation chamber through the drainage holes. The stain contaminated water collects at the bottom of the drain box 18 from whence it exits the mechanism through the drain pipe.

The microscopic slides which have been stained by various staining procedures are placed vertically in the slide tray rack. The bottom of the slide tray rack is open allowing water to flow up and down along the slide faces. When the slides are arranged in a side tray resting on the irrigation shelf inside the irrigation chamber the staining solution will be rinsed off of the slides by the force of the fresh water entering the irrigation chamber from below and rising upwards.

While preferred embodiments use quarter-inch plexiglass panels, other suitable materials may be used.

We claim:

1. A portable cleaning apparatus for rinsing water soluble stains from microscope slides comprising,
    rinsing chamber means for holding objects to be rinsed and for receiving rinsing fluid,
    fluid inlet means, disposed at a lower portion of the rinsing chamber means, for introducing rinsing fluid into the rinsing chamber,
    water circulating means, disposed around a perimeter and at a bottom portion of the rinse chamber means and further having apertures along a side portion towards a center of the apparatus along the entire water circulating means for circulating incoming rinsing fluid from a source of rinsing fluid,
    fluid outlet means, disposed at a lower portion of a draining chamber means, for releasing contaminant-bearing rinsing fluid to a drain,
    fluid passage means, disposed at an upper portion of the rinsing chamber means, for passing rinsing fluid from the rinsing chamber means to the draining chamber, and
    floor means for supporting microscope slides therein disposed in a bottom portion of the rinsing chamber means.

2. The apparatus of claim 1 wherein the rinsing chamber means is disposed within the draining chamber means.

3. The apparatus of claim 2 wherein the rinsing chamber means comprises a rinse chamber having sidewalls and a bottom.

4. The apparatus of claim 3 wherein the draining chamber means comprises a drain chamber means having sidewalls and a bottom.

5. The apparatus of claim 4 wherein the floor means comprises a grate disposed directly over the fluid circulating means and attached to the walls of the rinse chamber and having apertures for allowing the passage of rinsing fluid from the fluid circulating means into the rinse chamber.

6. The apparatus of claim 5 wherein the fluid passage means comprises holes disposed along the sidewalls of the rinse chamber means at an upper portion thereof.

7. The apparatus of claim 6 wherein a top flange is horizontally disposed and wherein sidewalls of the drain chamber means and rinse chamber means are substantially perpendicular to the top flange.

8. The apparatus of claim 7 wherein the sidewalls of the rinse chamber means are parallel to and spaced inwardly of the sidewalls of the drain chamber.

9. The apparatus of claim 4 comprising a top flange extending between tops of the drain chamber means and the rinse chamber, means thereby enclosing the drain chamber means and interconnecting the drain chamber means and rinse chamber means.

10. The apparatus of claim 1 further comprising a removable tray receivable in the rinsing chamber means.

11. The apparatus of claim 1 wherein the rinsing fluid is tap water from a sink and the apparatus is placed adjacent the sink during use and drains into a drain in the sink.

12. An apparatus for rinsing microscope slides with tap water from a sink and using a sink drain for disposal of the rinse water comprising,
- an inner box having a bottom and an open top through which slides are placed within the inner box.
- an outer box having larger dimensions than the inner box, wherein the inner box is disposed within the outer box,
- a top flange connected to upper edges of the inner and outer boxes, thereby interconnecting the inner and outer boxes,
- a fresh water inlet disposed at a bottom portion of the inner box and being connectable to a source of fresh water,
- a water conduit, connected to the fresh water inlet, disposed around a perimeter and at the bottom of the inner box and further having apertures along a side portion towards a center of the apparatus along the entire water conduit through which water enters the inner box,
- a contaminated water outlet disposed at a bottom portion of the outer box, and
- a plurality of draining ports disposed along an upper portion of the inner box for communicating water from the inner box to the outer box and out of the apparatus through the outlet, wherein the inner box is open to atmosphere and the outer box is closed.

13. The apparatus of claim 12 further comprising a shelf disposed directly over the water conduit and attached to the walls of the rinsing chamber and having apertures through which water passes from the water conduit, and having an upper surface supporting slides.

14. The apparatus of claim 12 wherein the inner and outer boxes are made of plexiglass panels.

15. The apparatus of claim 12 wherein the water conduit is made of PVC piping.

16. The apparatus of claim 15 wherein the sidewalls and bottom of the inner box are spaced inwardly from the sidewalls and bottom of the outer box.

17. A portable apparatus for rinsing microscope slides with tap water from a sink and using a sink drain for disposal of the rinse water comprising,
- a rinsing chamber having side walls, a bottom and an open top through which slides are placed within the rinsing chamber,
- a draining chamber having side walls, a bottom, and larger dimensions than the rinsing chamber, wherein the rinsing chamber is disposed within the draining chamber,
- an irrigation coil, disposed around a perimeter and at a bottom portion of the rinsing chamber and further having apertures along a side portion towards the center of the apparatus along the entire irrigation coil which circulates incoming tap water,
- a fresh water inlet disposed at the bottom of the rinsing chamber which connects the irrigation coil to a sink,
- a contaminated water outlet disposed at a bottom portion of the draining chamber,
- a plurality of drainage ports disposed along an upper portion of the rinsing chamber for communicating water from the rinsing chamber to the draining chamber and out of the apparatus through the outlet, wherein the inner box is open to atmosphere and the outer box is closed,
- a shelf disposed directly over the irrigation coil and attached to the walls of the rinsing chamber and having apertures through which water passes from the irrigation coil, and having upper surface supporting slides, and
- a top flange extending between tops of the draining chamber and the rinsing chamber, thereby enclosing the draining chamber and interconnecting the draining chamber and the rinsing chamber, wherein the top flange extends over the walls of the draining chamber by at least one-half inch, wherein the top flange is horizontally disposed and wherein side walls of the draining chamber and rinsing chamber are substantially perpendicular to the top flange, and wherein the side walls of the rinsing chamber are parallel to and spaced inwardly of the side walls of the draining chamber.

* * * * *